United States Patent
Boyadzhyan et al.

(10) Patent No.: US 10,509,016 B2
(45) Date of Patent: *Dec. 17, 2019

(54) METHODS FOR DETECTING LACOSAMIDE BY MASS SPECTROMETRY

(71) Applicant: Quest Diagnostics Investments Incorporated, Wilmington, DE (US)

(72) Inventors: Beatrisa Boyadzhyan, San Juan Capistrano, CA (US); Karin Thomassian, San Juan Capistrano, CA (US); Anita Dermartirosian, San Juan Capistrano, CA (US); Lou Jambor, San Juan Capistrano, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/787,439

(22) Filed: Oct. 18, 2017

(65) Prior Publication Data

US 2018/0224407 A1    Aug. 9, 2018

Related U.S. Application Data

(63) Continuation of application No. 15/388,741, filed on Dec. 22, 2016, now Pat. No. 9,823,227, which is a (Continued)

(51) Int. Cl.
*G01N 30/72*  (2006.01)
*G01N 33/94*  (2006.01)
(Continued)

(52) U.S. Cl.
CPC ....... *G01N 30/7266* (2013.01); *G01N 33/487* (2013.01); *G01N 33/9473* (2013.01);
(Continued)

(58) Field of Classification Search
CPC .... G01N 2560/00; G01N 33/48; G01N 33/49; G01N 33/68; G01N 33/6806;
(Continued)

(56) References Cited

U.S. PATENT DOCUMENTS 5,772,874 A   6/1998  Quinn et al.
5,795,469 A   8/1998  Quinn et al.
(Continued)

FOREIGN PATENT DOCUMENTS

WO    2011128079 A2    10/2011

OTHER PUBLICATIONS

Kim et al, "Liquid Chromatography Tandem Mass Spectometry for Quantification of Lacosamide, an Antiepileptic Drug, in Rat Plasma and Its Application to Pharmacokinetic Study", Biomed. Chomatogr. 2011 (Year: 2011)*

(Continued)

*Primary Examiner* — David E Smith
(74) *Attorney, Agent, or Firm* — Quest Diagnostics (57) ABSTRACT

Provided are methods for determining the amount of lacosamide in a sample using mass spectrometry. The methods generally involve ionizing lacosamide in a sample and detecting and quantifying the amount of the ion to determine the amount of lacosamide in the sample.

16 Claims, 8 Drawing Sheets

Related U.S. Application Data continuation of application No. 14/319,829, filed on Jun. 30, 2014, now Pat. No. 9,530,635, which is a continuation of application No. 13/339,267, filed on Dec. 28, 2011, now Pat. No. 8,779,355.

(51) Int. Cl.

| | | |
|---|---|---|
| H01J 49/00 | (2006.01) | |
| H01J 49/26 | (2006.01) | |
| G01N 33/487 | (2006.01) | |
| G01N 33/68 | (2006.01) | |
| G01N 33/48 | (2006.01) | |

(52) U.S. Cl.
CPC .......... *H01J 49/00* (2013.01); *H01J 49/0036* (2013.01); *H01J 49/26* (2013.01); *G01N 30/72* (2013.01); *G01N 33/48* (2013.01); *G01N 33/6812* (2013.01); *G01N 33/6848* (2013.01); *G01N 2560/00* (2013.01); *H01J 49/004* (2013.01); *Y10T 436/24* (2015.01); *Y10T 436/25375* (2015.01)

(58) Field of Classification Search
CPC .......... G01N 33/6812; G01N 33/6848; G01N 33/6851; G01N 33/94; G01N 33/9473; G01N 30/02; G01N 30/72; G01N 30/7266; G01N 33/487; H01J 49/00; H01J 49/0036; H01J 49/004; H01J 49/26; H01J 49/0095; Y10T 436/20; Y10T 436/200833; Y10T 436/24; Y10T 436/25; Y10T 436/25125; Y10T 436/25375; Y10T 436/255
USPC ..... 436/63, 86, 89, 106, 127, 128, 161, 173, 436/174, 175, 177, 178; 422/70, 89, 527, 422/533, 534; 250/282, 283, 285; 514/16.8, 255, 5, 547

See application file for complete search history.

(56) References Cited

U.S. PATENT DOCUMENTS

| | | | |
|---|---|---|---|
| 5,919,368 | A | 7/1999 | Quinn et al. |
| 5,968,367 | A | 10/1999 | Quinn et al. |
| 6,107,623 | A | 8/2000 | Bateman et al. |
| 6,124,137 | A | 9/2000 | Hutchens et al. |
| 6,204,500 | B1 | 3/2001 | Whitehouse et al. |
| 6,268,144 | B1 | 7/2001 | Koester |
| 8,779,355 | B2 | 7/2014 | Boyadzhyan et al. |
| 9,530,635 | B2 | 12/2016 | Boyadzhyan et al. |
| 9,823,227 | B2 * | 11/2017 | Boyadzhyan ...... G01N 33/9473 |
| 2009/0241205 | A1 | 9/2009 | Beyreuther et al. |
| 2011/0251131 | A1 | 10/2011 | Masse |
| 2011/0263899 | A1 | 10/2011 | Bouvy et al. |
| 2011/0301238 | A1 | 12/2011 | Borges |
| 2013/0143792 | A1 | 6/2013 | Cunningham |
| 2013/0210837 | A1 | 8/2013 | Csjernyik et al. |
| 2013/0224151 | A1 | 8/2013 | Pearson et al. |
| 2013/0251813 | A1 * | 9/2013 | Cawello ............... A61K 9/1635 424/490 |

OTHER PUBLICATIONS

Kim et al, "Liquid Chromatography Tandem Mass Spectrometry for Quantification of Lacosamide, an Antiepileptic Drug, in Rat Plasma and its Application to Pharmacokinetic Study", Biomed. Chromatogr. 2011 (Year: 2011).*

Ben-Menachem E., et al., "Efficacy and Safety of Oral Lacosamide as Adjunctive Therapy in Adults with Partial-Onset Seizures," Epilepsia, 2007, vol. 48 (7), pp. 1308-1317.

Cada D.J., et al., "Lacosamide," Hospital Pharmacy, 2009, vol. 44 (6), pp. 497-508.

Cawello W., et al., "No Pharmacokine Interaction between Lacosamide and Carbamazepine in Healthy Volunteers," Journal of Clinical Pharmacology, 2010, vol. 50 (4), pp. 459-471.

Errington A.C., et al., "The Investigational Anticonvulsant Lacosamide Selectively Enhances Slow Inactivation of Voltage-Gated Sodium Channels," Molecular Pharmacology, 2008, vol. 73 (1), pp. 157-169.

Final Office Action dated Feb. 25, 2016 for U.S. Appl. No. 14/319,829, filed Jun. 30, 2014.

Halasz P., et al., "Adjunctive Lacosamide for Partial-Onset Seizures: Efficacy and Safety Results from a Randomized Controlled Trial," Epilepsia, 2009, vol. 50 (3), pp. 443-453.

Kim S.J., et al., "Liquid Chromatography-Tandem Mass Spectrometry for Quantification of Lacosamide, an Antiepileptic Drug, in Rat Plasma and Its Application to Pharmacokinetic Study," Biomedical Chromatography, 2012, vol. 26 (3), pp. 371-376.

Merchant M., et al., "Recent Advancements in Surface-Enhanced Laser Desorption/Ionization-Time of Flight-Mass Spectrometry," Electrophoresis, 2000, vol. 21 (6), pp. 1164-1167.

"Non-Final Office Action dated Mar. 15, 2017 for U.S. Appl. No. 15/388,741, filed Dec. 22, 2016."

Non-Final Office Action dated Sep. 19, 2013 for U.S. Appl. No. 13/339,267, filed Dec. 28, 2011.

Non-Final Office Action dated Jan. 22, 2016 for U.S. Appl. No. 14/063,956, filed Oct. 25, 2013.

Non-Final Office Action dated Jul. 22, 2015 for U.S. Appl. No. 14/319,829, filed Jun. 30, 2014.

Polson C., et al., "Optimization of Protein Precipitation Based Upon Effectiveness of Protein Removal and Ionization Effect in Liquid Chromatography-Tandem Mass Spectrometry," Journal of Chromatography B, 2003, vol. 785 (2), pp. 263-275.

Robb D.B., et al., "Atmospheric Pressure Photoionization: An Ionization Method for Liquid Chromatography—Mass Spectrometry," Analytical Chemistry, 2000, vol. 72 (15), pp. 3653-3659.

Sheets P.L., et al., "Differential Block of Sensory Neuronal Voltage-Gated Sodium Channels by Lacosamide [(2R)-2-(Acetylamino)-N-benzyl-3-methoxypropanamide], Lidocaine, and Carbamazepine," Journal of Pharmacology and Experimental Therapeutics, 2008, vol. 326 (1), pp. 89-99.

Wright Jr., G.L., et al., "Proteinchip Surface Enhanced Laser Desorption/Inization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.

Ziegler D., et al., "Efficacy and Safety of Lacosamide in Painful Diabetic Neuropathy," Diabetes Care, 2010, vol. 33 (4), pp. 839-841.

Zimmer D., et al., "Comparison of Turbulent-Flow Chromatography with Automated Solid-Phase Extraction in 96-Well Plates and Liquid-Liquid Extraction Used as Plasma Sample Preparation Techniques for Liquid Chromatography-Tandem Mass Spectrometry," Journal of Chromatography A, 1999, vol. 854, pp. 23-35.

Aguera A., et al., "One-year Routine Application of a New Method Based on Liquid . . . ," Journal of Chromatography A, 2004, vol. 1045, pp. 125-135.

Fiehn O., et al., "Mass Spectrometry: Quantitation," Encyclopedic Reference of Genomics and Proteomics in Molecular Medicine, 2006, pp. 1030-1034.

Jessome L., et al., "Ion Suppression: A Major Concern in Mass Spectrometry," LCGC North Ameerica, 2006, vol. 24 (5), pp. 498-510.

* cited by examiner

Figure 1. Exemplary Chromatograms of Lacosamide and Internal Standard

Figure 1C. Exemplary Chromatograms of Lacosamide Product Ions 251.0/91.0 and 251.0/108.0 and Internal Standard Lacosamide-d3 254.0/91.0

Figure 1D. Graph of Spectrum Intensity for Lacosamide Product Ions 251.0/91.0 and 251.0/108.0 and Internal Standard Lacosamide-d3 254.0/91.0

FIG. 2

Figure 3A. Lacosamide Q3 product ion scan spectra at CE 20V

Figure 3B. Lacosamide Q3 Product Ion Scan Spectrum at CE 35V

Figure 4. Linearity – Typical Calibration Curve

Figure 5. Specimen Type Comparison

METHODS FOR DETECTING LACOSAMIDE BY MASS SPECTROMETRY

CROSS REFERENCE TO RELATED APPLICATIONS

This application is a continuation of U.S. application Ser. No. 15/388,741, filed Dec. 22, 2016, now U.S. Pat. No. 9,823,227, issued on Nov. 21, 2017, which is a continuation of U.S. application Ser. No. 14/319,829, filed Jun. 30, 2014, now U.S. Pat. No. 9,530,635, issued on Dec. 27, 2016, which is a continuation of U.S. application Ser. No. 13/339,267, filed Dec. 28, 2011, now U.S. Pat. No. 8,779,355, issued on Jul. 15, 2014, each of which is incorporated by reference herein in its entirety.

FIELD OF THE INVENTION

The invention relates to the detection of lacosamide. In a particular aspect, the invention relates to methods for detecting lacosamide by mass spectrometry.

BACKGROUND OF THE INVENTION

The following description of the background of the invention is provided simply as an aid in understanding the invention and is not admitted to describe or constitute prior art to the invention.

Lacosamide (also known as Vimpat™, erlosamide, and harkoseride) is a functionalized amino acid that is used as an adjunctive therapy the treatment of partial-onset seizures (Halasz et al., Epilepsia, 50(3):443-453, 2009). Lacosamide is also being investigated as a treatment for diabetic neuropathic pain (Ziegler et al. Diabetes Care. 2010 April; 33(4): 839-41). Lacosamide has dual mechanisms of action. In one mechanism, lacosamide selectively enhances slow inactivation of voltage-gated sodium channels, which in turn stabilizes hyperexcitable neuronal membranes and inhibits neuronal firing (Sheets et al., J Pharmacol Exp Ther. 2008 July; 326(1):89-99; Errington et al., Mol Pharmacol. 2008 January; 73(1):157-69). In another mechanism of action, lacosamide modulates collapsin response mediator protein-2 (CRMP-2), a protein that has altered expression in epilepsy and other neurodegenerative diseases (Cada et al., Hospital Pharmacy 2009 June; 44(6), 497-508).

Assays for lacosamide blood levels have been developed and are used by patients and physicians to optimize therapeutic dosages.

SUMMARY OF THE INVENTION

The present invention provides methods for detecting the amount of lacosamide in a sample by mass spectrometry, including tandem mass spectrometry.

In one aspect, methods are provided for determining the amount of lacosamide in a sample. Methods of this aspect include: (a) ionizing lacosamide from the sample to produce one or more lacosamide ions detectable by mass spectrometry, wherein the ions comprise one or more ions selected from the group consisting of ions with a mass/charge ratio of 251.0±0.5, 91.0±0.5, and 108.0±0.5; (b) determining the amount of one or more lacosamide ions by mass spectrometry; and (c) using the amount of the lacosamide ion(s) to determine the amount of lacosamide in the sample. In some embodiments, the mass spectrometry is tandem mass spectrometry. In some embodiments, the methods further include purifying lacosamide in the sample prior to mass spectrometry. In some embodiments, purifying includes purifying with liquid chromatography. In related embodiments, the liquid chromatography comprises high performance liquid chromatography (HPLC). In some embodiments, purifying includes one or more purification steps followed by liquid chromatography. In related embodiments, the one or more purification steps prior to liquid chromatography include protein precipitation. In some embodiments, the sample is generated by subjecting a body fluid to one or more processing steps. In some embodiments, the sample is generated by subjecting plasma or serum to one or more processing steps. In some embodiments, ionizing includes generating a lacosamide precursor ion with a mass/charge ratio of 251.0±0.5, and generating one or more lacosamide fragment ions selected from the group consisting of ions with a mass/charge ratio of 91.0±0.5 and 108.0±0.5. In some embodiments, ionizing is conducted in positive ion mode. In some embodiments, the method has a lower limit of quantitation within the range of 20 µg/ml and 0.5 µg/ml, inclusive.

In a second aspect, methods are provided for determining the amount of lacosamide in a body fluid sample by tandem mass spectrometry. Methods of this aspect include: (a) ionizing lacosamide, purified from the body fluid sample by liquid chromatography, to generate a lacosamide precursor ion having a mass/charge ratio of 251.0±0.5; (b) producing one or more lacosamide fragment ions of the lacosamide precursor ion, wherein at least one of the one or more lacosamide fragment ions comprise an ion selected from the group of ions having a mass/charge ratio of 91.0±0.5 and 108.0±0.5; and (c) determining the amount of one or more of the ions generated in step (b) or (c) or both and relating the determined ions to the amount of lacosamide in the body fluid sample. In some embodiments, the methods have a lower limit of quantitation within the range of 20 µg/ml and 0.5 µg/ml, inclusive. In some embodiments, the liquid chromatography includes high performance liquid chromatography (HPLC). In some embodiments, the lacosamide purified from a body fluid sample is purified by one or more purification steps followed by liquid chromatography. In related embodiments, the one or more purification steps prior to liquid chromatography include protein precipitation. In some embodiments, the body fluid sample includes plasma or serum. In some embodiments, ionization is conducted in positive ion mode.

As used herein, unless otherwise stated, the singular forms "a," "an," and "the" include plural reference. Thus, for example, a reference to "a protein" includes a plurality of protein molecules.

As used herein, the term "processing step" refers to any sample handling step without limitation, including, for example: heating, cooling, centrifugation, or purification by any method known in the art. In particular, purification steps may include one or more of filtration, protein precipitation, liquid-liquid extraction, solid-phase extraction, liquid chromatography (including high performance liquid chromatography), and the like.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected lacosamide parent or daughter ions by mass spectrometry. Relative reduction as this term is used does not require that any substance, present with the analyte of interest in the material to be purified, is entirely removed by purification.

As used herein, the term "sample" refers to any sample that may contain lacosamide. As used herein, the term "body fluid" means any fluid that can be isolated from the body of an individual. For example, "body fluid" may include blood, plasma, serum, bile, saliva, urine, tears, perspiration, and the like.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and high turbulence liquid chromatography (HTLC).

As used herein, the term "high performance liquid chromatography" or "HPLC" refers to liquid chromatography in which the degree of separation is increased by forcing the mobile phase under pressure through a stationary phase on a support matrix, typically a densely packed column.

As used herein, the term "high turbulence liquid chromatography" or "HTLC" refers to a form of chromatography that utilizes turbulent flow of the material being assayed through the column packing as the basis for performing the separation. HTLC has been applied in the preparation of samples containing two unnamed drugs prior to analysis by mass spectrometry. See, e.g., Zimmer et al., *J. Chromatogr. A* 854: 23-35 (1999); see also, U.S. Pat. Nos. 5,968,367, 5,919,368, 5,795,469, and 5,772,874, which further explain HTLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 35 μm, such as greater than about 50 μm.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means±10%. In a preferred embodiment the analytical column contains particles of about 5 μm in diameter.

As used herein, the term "on-line" or "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000).

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. Robb, D. B., Covey, T. R. and Bruins, A. P. (2000): See, e.g., Robb et al., Atmospheric pressure photoionization: An ionization method for liquid chromatography-mass spectrometry. Anal. Chem. 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "limit of quantitation" or "LOQ" refers to the point where measurements become quantitatively meaningful. The analyte response at this LOQ is identifiable, discrete and reproducible and is calculated as the mean plus 10 standard deviations (SD).

As used herein, the term "limit of detection" or "LOD" is the point at which the measured value is larger than the uncertainty associated with it. The LOD is the point at which a value is beyond the uncertainty associated with its measurement and is defined as four standard deviations from the zero concentration.

As used herein, an "amount" of lacosamide in a body fluid sample refers generally to an absolute value reflecting the mass of lacosamide detectable in volume of body fluid. However, an amount also contemplates a relative amount in comparison to another lacosamide amount. For example, an amount of lacosamide in a body fluid can be an amount which is greater than a control or normal level of lacosamide normally present.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

DETAILED DESCRIPTION OF THE INVENTION

Methods of the present invention are described for measuring the amount of lacosamide in a sample. More specifically, mass spectrometric methods are described for detecting and quantifying lacosamide in a sample. The methods may utilize liquid chromatography (LC), preferably HPLC, to perform a purification of selected analytes, and combine this purification with unique methods of mass spectrometry (MS), thereby providing a high-throughput assay system for detecting and quantifying lacosamide in a sample. The embodiments are particularly well suited for application in large clinical laboratories for automated lacosamide assay.

Suitable samples for use in methods of the present invention include any sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Particularly preferred samples include bodily fluids such as blood, plasma, serum, saliva, cerebrospinal fluid, or a tissue sample. Such samples may be obtained, for example, from a patient; that is, a living person, male or female, presenting oneself in a clinical setting for diagnosis, prognosis, or treatment of a disease or condition. The test sample is preferably obtained from a patient, for example, blood serum or plasma.

The present invention contemplates kits for a lacosamide quantitation assay. A kit for a lacosamide quantitation assay of the present invention may include a kit comprising an internal standard in amounts sufficient for at least one assay. Typically, the kits will also include instructions recorded in a tangible form (e.g., contained on paper or an electronic medium) for using the packaged reagents for use in a measurement assay for determining the amount of lacosamide.

Calibration and QC pools for use in embodiments of the present invention can be prepared using plasma or serum that has been spiked with lacosamide. All sources of human or non-human plasma or serum to be used in calibration and QC pools should be checked to ensure that they do not contain measurable amounts of lacosamide.

Sample Preparation for Mass Spectrometry

Biological and non-biological samples at or near room temperature typically do not require any temperature adjustment. Frozen or refrigerated samples (including controls) are typically thawed and brought to or near room temperature rapidly. Internal standard may be added to frozen samples once they are thawed.

Optionally, samples may be prepared for mass spectrometry by subjecting the sample to one or more methods to enrich lacosamide relative to other components in the sample (e.g. protein). Various methods may be used to enrich lacosamide relative to other components in the sample (e.g. protein) prior mass spectrometry, including for example, liquid-liquid extraction (e.g., ethyl acetate extraction and methanol extraction), solid-phase extraction, liquid chromatography, filtration, centrifugation, thin layer chromatography (TLC), electrophoresis including capillary electrophoresis, affinity separations including immunoaffinity separations, and the use of chaotropic agents or any combination of the above or the like.

Protein precipitation is one preferred method of preparing a test sample, especially a biological test sample, such as serum or plasma. Such protein purification methods are well known in the art, for example, Polson et al., *Journal of Chromatography B* 785:263-275 (2003), describes protein precipitation techniques suitable for use in methods of the present invention. Protein precipitation may be used to remove most of the protein from the sample leaving lacosamide in the supernatant. The samples may be centrifuged to separate the liquid supernatant from the precipitated proteins; alternatively the samples may be filtered, for example through a glass fiber filter, to remove precipitated proteins. The resultant supernatant or filtrate may then be applied directly to mass spectrometry analysis; or alternatively to liquid chromatography and subsequent mass spectrometry analysis. In certain embodiments, the use of protein precipitation such as for example, methanol protein precipitation, may obviate the need for high turbulence liquid chromatography (HTLC) or other on-line extraction prior to mass spectrometry or HPLC and mass spectrometry.

Accordingly, in some embodiments, the method involves (1) performing a protein precipitation of the sample of interest; and (2) loading the supernatant directly onto the LC-mass spectrometer without using on-line extraction or high turbulence liquid chromatography (HTLC).

In some embodiments, HTLC, alone or in combination with one or more purification methods, may be used to purify lacosamide prior to mass spectrometry. In such embodiments samples may be extracted using an HTLC extraction cartridge which captures the analyte, then eluted and chromatographed on a second HTLC column or onto an analytical HPLC column prior to ionization. Because the steps involved in these chromatography procedures may be linked in an automated fashion, the requirement for operator involvement during the purification of the analyte can be minimized. This feature may result in savings of time and costs, and eliminate the opportunity for operator error.

One means of sample purification that may be used prior to mass spectrometry is liquid chromatography (LC). Liquid chromatography, including high-performance liquid chromatography (HPLC), relies on relatively slow, laminar flow technology. Traditional HPLC analysis relies on column packing in which laminar flow of the sample through the column is the basis for separation of the analyte of interest from the sample. The skilled artisan will understand that separation in such columns is a diffusion process and may select HPLC instruments and columns that are suitable for use with lacosamide. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, C-12, or C-18 bonded alkyl groups. Alternatively, a suitable surface is a base-deactivated biphenyl silica surface, such as found in a Pinnacle® DB Biphenyl HPLC column. The chromatographic column includes an inlet port for receiving a sample directly or indirectly from coupled SPE column and an outlet port for discharging an effluent that includes the fractionated sample.

In one embodiment, the sample may be applied to the column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one embodiment, HPLC is conducted with a hydrophobic column chromatographic system. In certain preferred embodiments, a Pinnacle® DB Biphenyl analytical column (50×2.1 mm, 5 µl column or equivalent) is used. In certain preferred embodiments, HTLC and/or HPLC are performed using HPLC Grade 0.1% formic acid in methanol and Grade 0.1% formic acid in water as the mobile phases.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

Detection and Quantitation by Mass Spectrometry

In various embodiments, lacosamide present in a test sample may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

In preferred embodiments, lacosamide is ionized by ESI in positive ion mode. In related preferred embodiments, lacosamide ion is in a gaseous state and the inert collision gas is argon or nitrogen; preferably nitrogen.

In mass spectrometry techniques generally, after the sample has been ionized the positively charged or negatively charged ions thereby created may be analyzed to determine a mass-to-charge ratio. Suitable analyzers for determining mass-to-charge ratios include quadrupole analyzers, ion traps analyzers, magnetic and electric sector analyzers, and time-of-flight analyzers. The ions may be detected using several detection modes. For example, selected ions may be detected, i.e. using a selective ion monitoring mode (SIM), or alternatively, ions may be detected using a scanning mode, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion is subsequently fragmented to yield one or more fragment ions (also called daughter or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

The mass spectrometer typically provides the user with an ion scan; that is, the relative abundance of each ion with a particular mass/charge over a given range (e.g., 100 to 1000 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule.

Alternatively, standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of lacosamide. Methods of generating and using such standard curves are well known in the art and one of ordinary skill is capable of selecting an appropriate internal standard. For example, an isotopically labeled lacosamide may be used as an internal standard; in certain preferred embodiments the standard is lacosamide-D3. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activation dissociation is often used to generate the fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In particularly preferred embodiments, lacosamide is detected and/or quantified using MS/MS as follows. The samples are subjected to protein precipitation followed by liquid chromatography, preferably HPLC; the flow of liquid solvent from the chromatographic column enters the heated nebulizer interface of an MS/MS analyzer; and the solvent/analyte mixture is converted to vapor in the heated tubing of the interface. The analyte (e.g., lacosamide), contained in the nebulized solvent, is ionized by the corona discharge needle of the interface, which applies a large voltage to the nebulized solvent/analyte mixture. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for ions with the mass to charge ratios of a particular lacosamide precursor ion. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with a neutral collision gas, e.g. nitrogen, and fragment. This process is called collision activated dissociation (CAD). The lacosamide fragment ions are passed into quadrupole 3 (Q3), where particular lacosamide fragment ions are allowed to pass to the detector while other ions are eliminated.

The methods may involve MS/MS performed in either positive or negative ion mode; preferably positive ion mode. Using standard methods well known in the art, one of ordinary skill is capable of identifying one or more fragment ions of a particular precursor ion of lacosamide that may be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods. The areas under the peaks corresponding to particular ions, or the amplitude of such peaks, are measured and the area or amplitude is correlated to the amount of the analyte of interest. In certain embodiments, the area under the curves, or amplitude of the peaks, for fragment ion(s) and/or precursor ions are measured to determine the amount of lacosamide. As described above, the relative abundance of a given ion may be converted into an absolute amount of the original analyte, e.g., lacosamide, using calibration standard curves based on peaks of one or more ions of an internal molecular standard, such as lacosamide-D3.

The following examples serve to illustrate the invention. These examples are in no way intended to limit the scope of the methods.

EXAMPLES

Example 1: Sample (Plasma and Serum) and Reagent Preparation

Plasma samples were prepared by collecting blood in a Vacutainer® tube with sodium heparin and refrigerating to about 2° C. to 8° C. Samples were then centrifuged (about 2200-2500 rpm, about 800-1000 g) for about 8 to 10 minutes while maintaining refrigeration at about 2° C. to 8° C. The supernatants from the centrifugation were poured off and collected for later analysis.

Serum samples were prepared by collecting blood in a Vacutainer® tube with no additives and allowed to clot for 20 to 30 minutes while refrigerated at about 2° C. to 8° C. The samples were then centrifuged (about 2200-2500 rpm, about 800-1000 g) for about 8 to 10 minutes while maintaining refrigeration at about 2° C. to 8° C. The resulting serum was then transferred as above for plasma.

Lacosamide and Lacosamide-D3 (internal standard) stock solutions were prepared. Lacosamide or lacosamide-D3 powders were mixed with methanol in separate glass vials. Aliquots of stock solutions were kept frozen.

Internal standard working solution of lacosamide-D3 (5 µg/ml) was prepared by diluting lacosamide-D3 stock solution in methanol to the desired concentration. Standard working solution of lacosamide (200 µg/ml) was prepared by diluting lacosamide stock solution in 50% methanol to the desired concentration. Serum samples spiked with various concentrations of lacosamide were prepared by diluting the 200 µg/ml lacosamide standard working solution with drug-free serum. For example, serum having 20 µg/ml of lacosamide was prepared by diluting the lacosamide working standard 1:10 in drug-free serum. The following working stocks of lacosamide in serum were prepared: 20 µg/ml (1:10), 10 µg/ml (1:20), 8 µg/ml (1:25), 4 µg/ml (1:50), 2 µg/ml (1:100), 1 µg/ml (1:200), and 0.5 µg/ml (1:400).

Low level (about 2.5 µg/ml), medium level (about 5 µg/ml), and high level (about 12 µg/ml) lacosamide controls custom ordered from UTAK Laboratories were also used. The three levels of lacosamide controls were mixed from drug-free serum (Bio-Rad #456) spiked with stock solutions of lacosamide and lacosamide-D3.

Example 2: Extraction of Lacosamide from Plasma and Serum Using Liquid Chromatography Liquid chromatography (LC) samples were prepared by thawing standards, controls, and patient samples to room temperature. Proteins were precipitated from 100 µl of each of the standards, controls, and patient samples by adding 200 µl methanol and 20 µl of internal standard, vortexing for about 30 seconds, and then centrifuging for about 5 minutes at about 14,000 g. The clear supernatant was then removed and poured into the autosampler vials with flat bottom glass inserts for insertion into an autosampler cooling unit.

Sample injection was performed with a Agilent 1200 series pump system operating in laminar flow mode using Analyst v. 1.5 or newer software. 50% methanol in water was used as an autosampler wash solution.

The HPLC system automatically injected about 10 µL of the above prepared samples standards and controls into a Restek guard column (catalog #940950212) followed by an HPLC analytical column (Pinnacle® DB Biphenyl, 50×2.1 mm, 5 µm column).

A binary HPLC gradient was applied to the analytical column to separate lacosamide from other analytes contained in the sample. Mobile phase A was 0.1% formic acid in methanol and mobile phase B was 0.1% formic acid in water. A gradient program was used to elute and separate the components from each other and reduce the presence of compounds likely to cause ion suppression. First, a mixture of 10% mobile phase A/90% mobile phase B was applied to the column for 0.1 minutes. Then, the solvent mixture was stepped to 70% mobile phase A/30% mobile phase B for 0.1 minutes. This was followed by a linear ramp to 90% mobile phase A/10% mobile phase B over 1.7 minutes, during which time the analyte eluted from the column. Finally, the solvent mixture was stepped back to 10% mobile phase A/90% mobile phase B for 0.1 minutes to flush the column. The gradient times, flow rates and solution percentages are listed in Table 1 below.

TABLE 1

Gradient Program

| Step | Total Time (min) | Flow Rate (µl/min) | A (%) [Organic] | B (%) [Aqueous] | Transition |
|---|---|---|---|---|---|
| 0 | 0.10 | 750 | 10 | 90 | Step |
| 1 | 0.20 | 750 | 70 | 30 | Step |
| 2 | 1.90 | 750 | 90 | 10 | Ramp |
| 3 | 2.00 | 750 | 10 | 90 | Step |

The separated sample was then subjected to MS/MS for quantitation of lacosamide.

Example 3: Detection and Quantitation of Lacosamide by MS/MS

MS/MS was performed using an API 3200 system (Applied Biosystems). The software program Analyst 1.5 from Applied Biosystems was used in the Examples described herein. Liquid solvent/analyte exiting the analytical HPLC column flowed to the electro-spray ionization interface of the API 3200 system where the analyte was ionized in positive ion mode.

Ions passed to the first quadrupole (Q1), which selected ions with a mass to charge ratio of 251.0±0.5 m/z. Ions entering Quadrupole 2 (Q2) collided with nitrogen gas to generate ion fragments, which were passed to quadrupole 3 (Q3) for further selection. Simultaneously, the same process using isotope dilution mass spectrometry was carried out with an internal standard, lacosamide-D3. A second transition is monitored to provide a qualifying ion ratio to ensure analyte identity. The mass transitions listed in Table 2 were used for detection and quantitation during validation on positive polarity.

TABLE 2

Mass Transitions for Lacosamide

| Substance | Q1 (m/z) | Q3 (m/z) and CE (V) | Q3 qualifier (m/z) and CE (V) |
|---|---|---|---|
| Lacosamide | 251.0 | 91.0 (at 35 V) | 108.0 (at 20 V) |
| Lacosamide-D3 | 254.0 | 91.0 (at 35 V) | — |

Figure 1A:
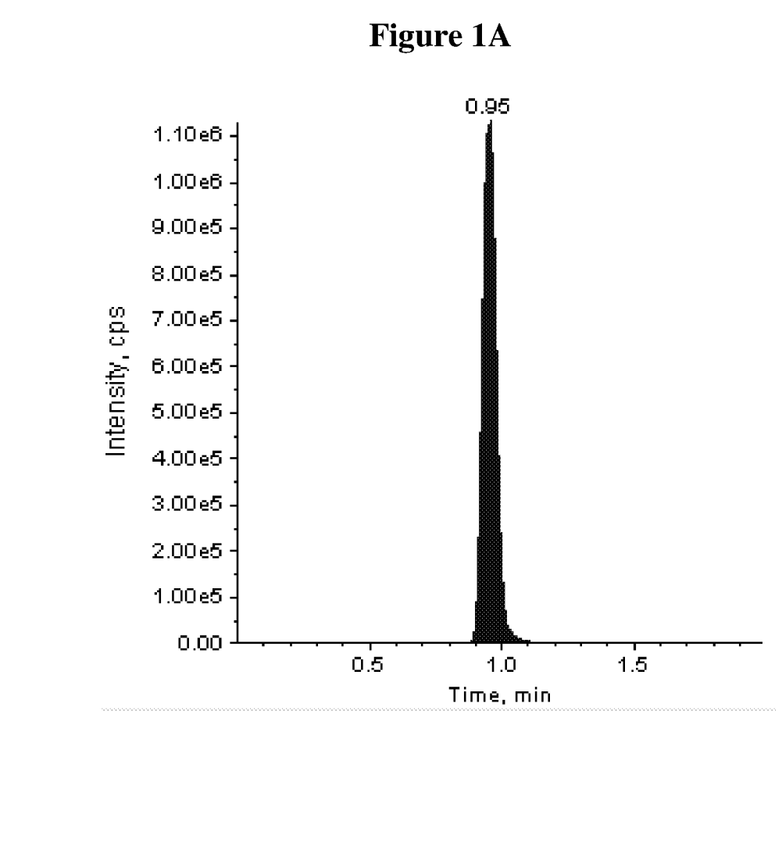
FIGS. 1A and 1B show exemplary chromatograms of 91 m/z fragment ions from lacosamide and lacosamide-D3, respectively.
Figure 1B:
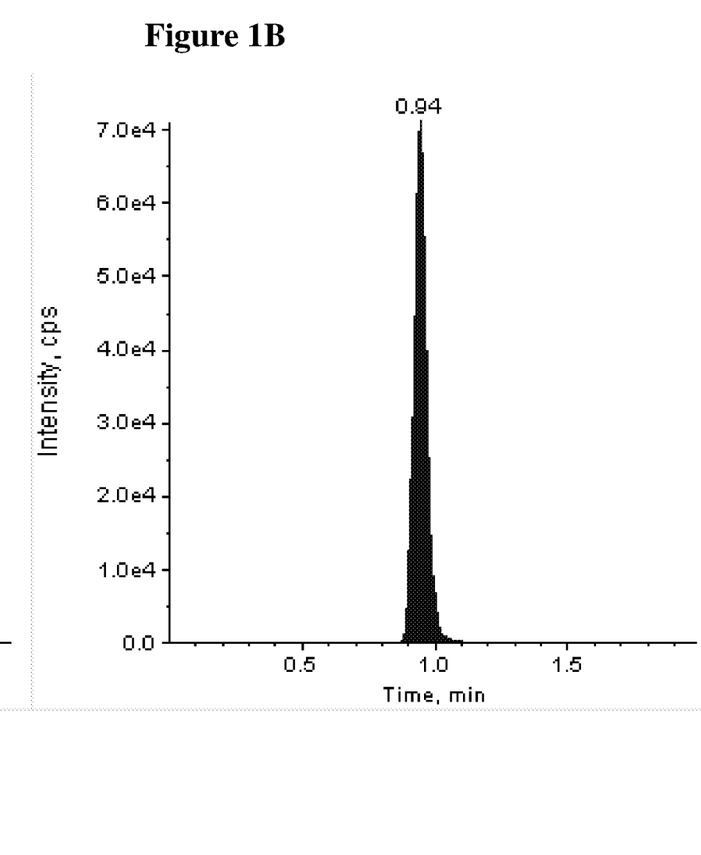
Figure 1C:
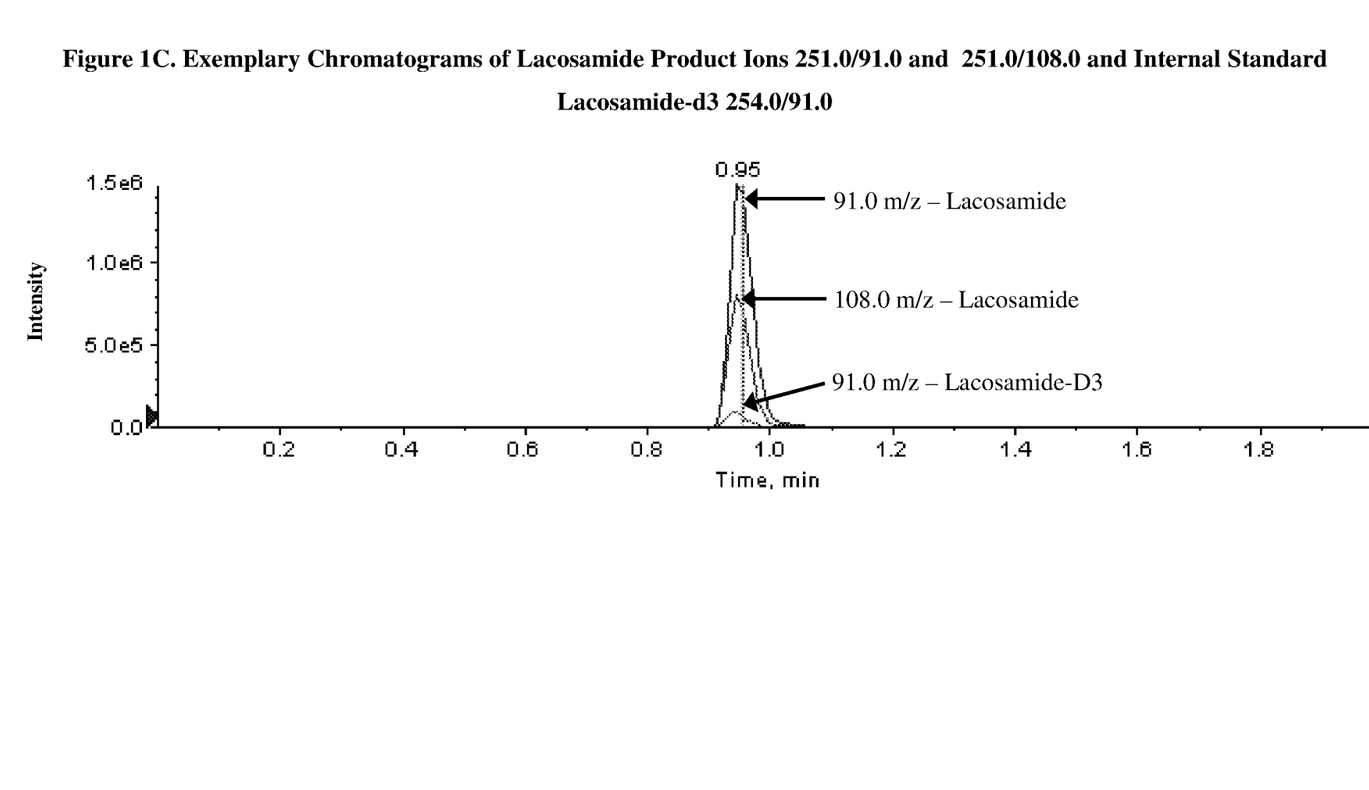
FIG. 1C is an overlay of exemplary chromatograms of 91.0 m/z and 108.0 m/z fragment ions from lacosamide and 91 m/z fragment ions from lacosamide-D3.
Figure 1D:
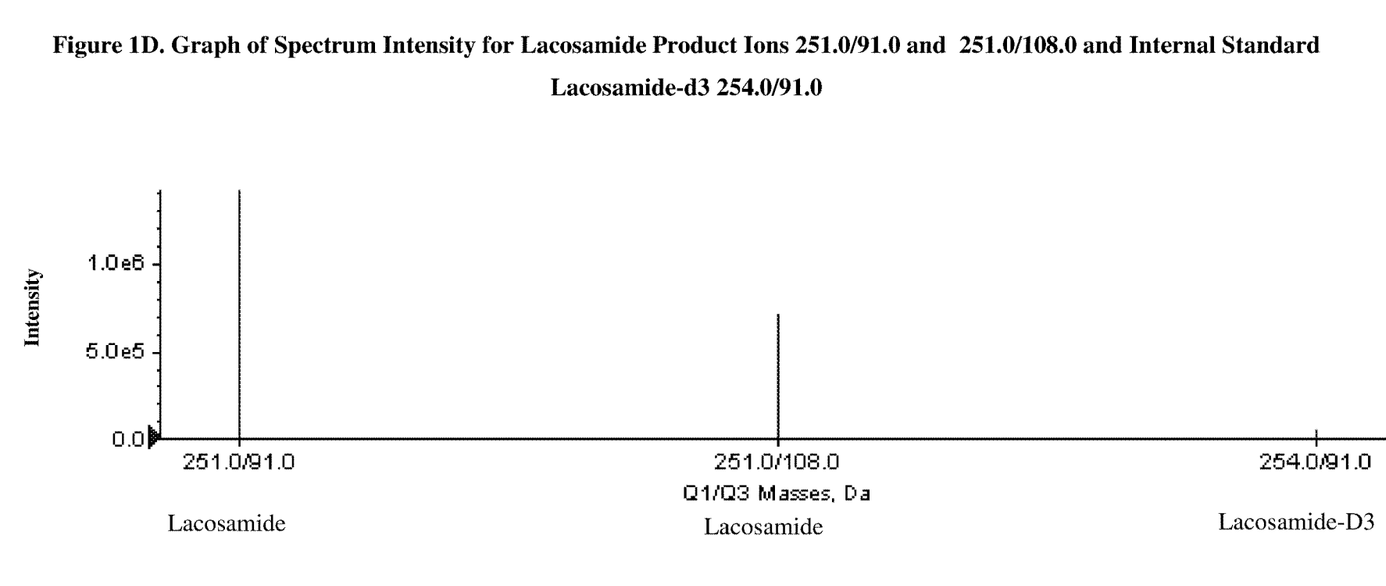
FIG. 1D is a chart showing the chromatogram intensities of 91.0 m/z and 108.0 m/z fragment ions from lacosamide and 91 m/z fragment ions from lacosamide-D3. Details are discussed in Example 3.

Exemplary chromatograms for lacosamide and lacosamide-D3 (internal standard) are found in FIGS. 1A, 1B, and 1C.

Figure 2:
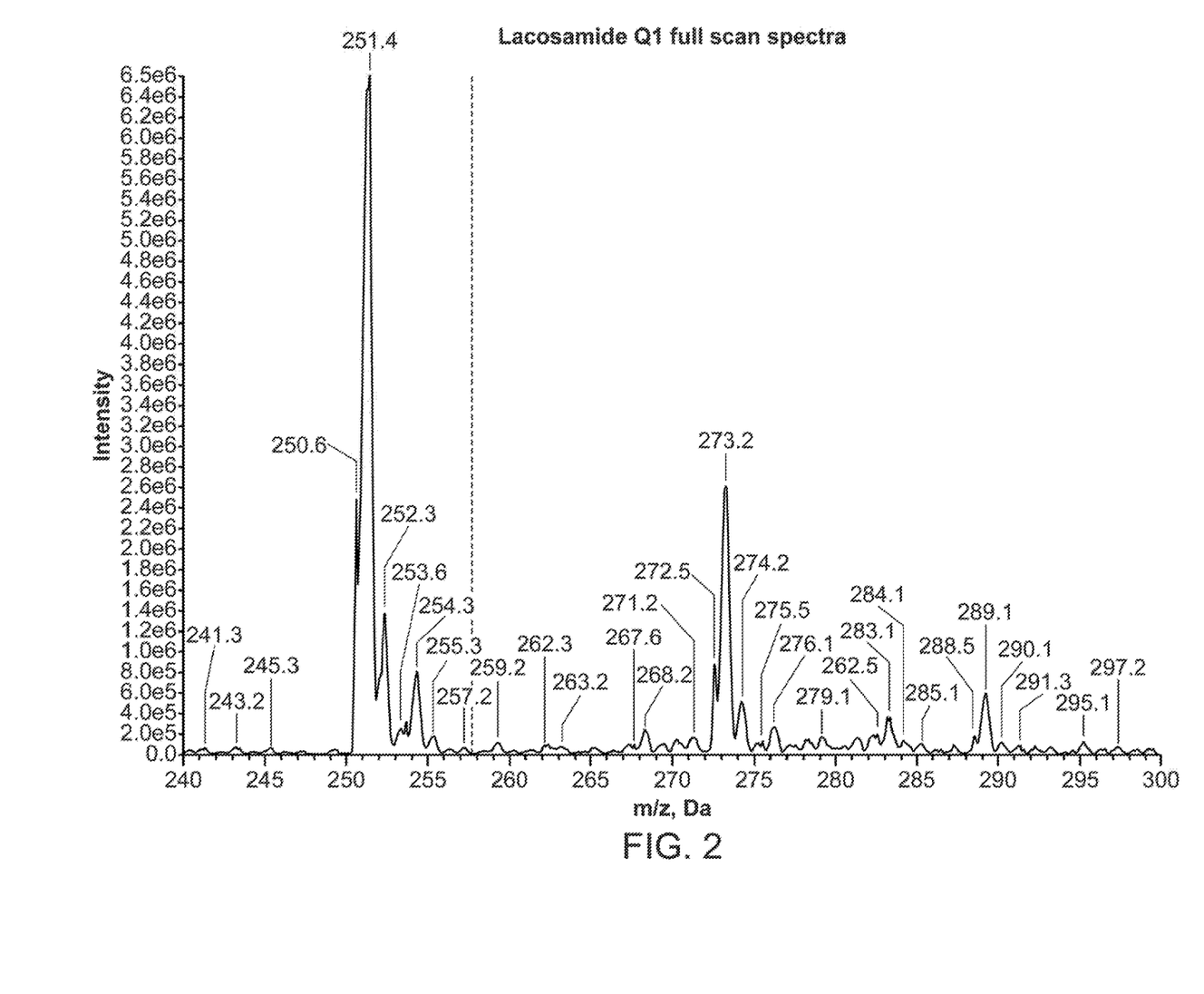
FIG. 2 shows Q1 full scan spectra for lacosamide. Details are discussed in Example 3
Figure 3A:
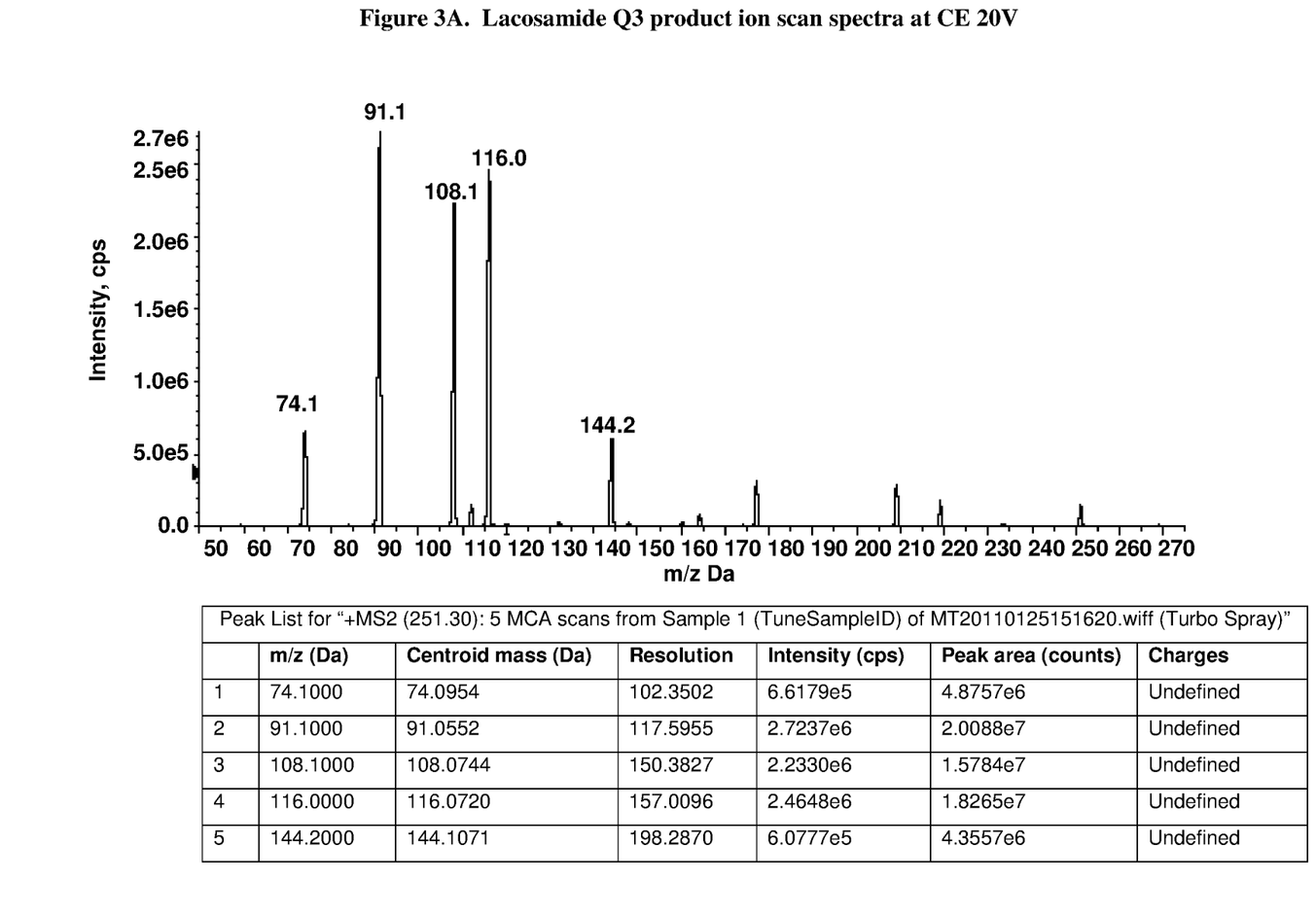
FIG. 3A shows Q3 product ion scan spectra for fragmentation of lacosamide with a mass/charge ratio of 251.0±0.5 at a collision energy of 20 V.
Figure 3B:
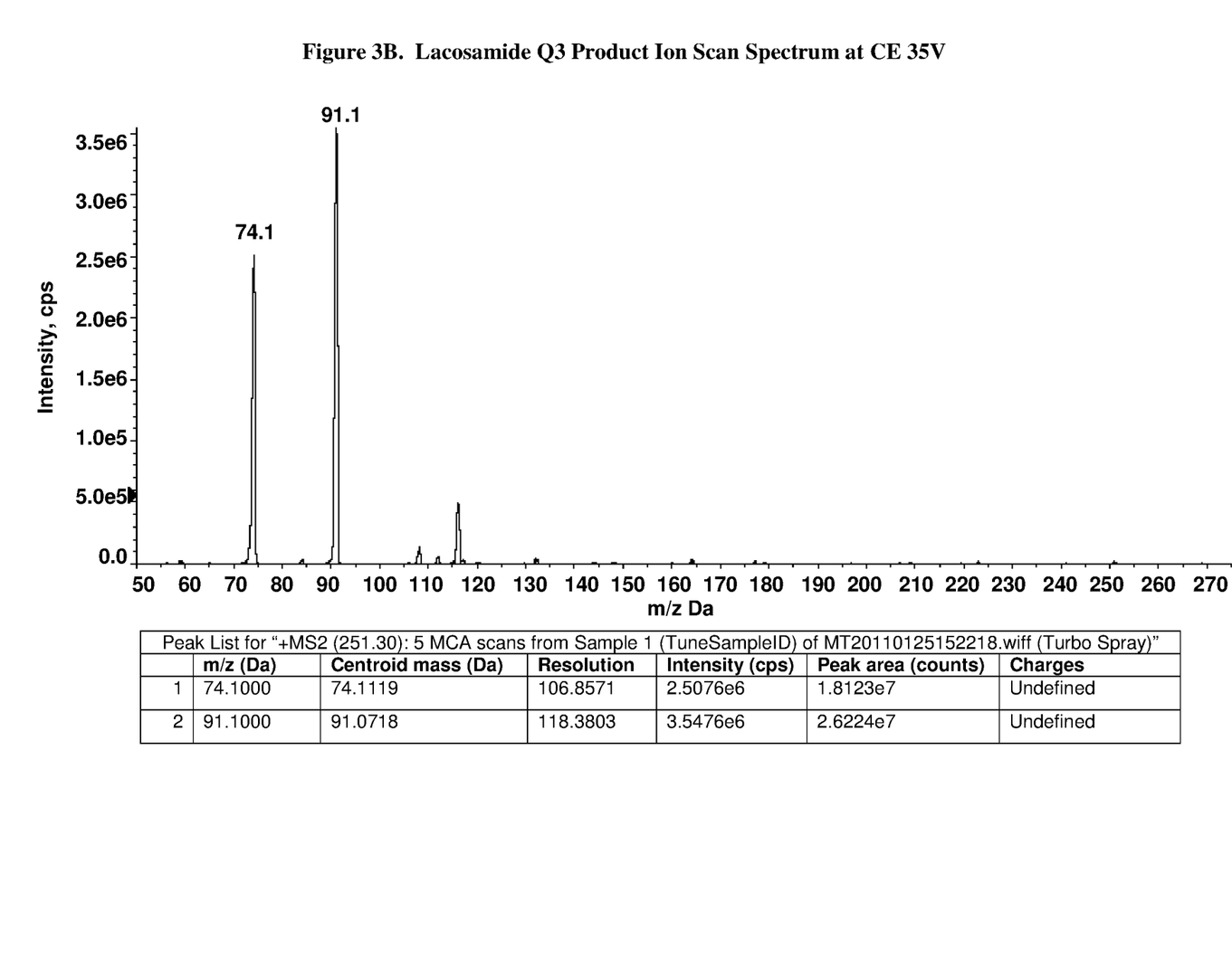
FIG. 3B shows Q3 product ion scan spectra for the same lacosamide precursor ion at a collision energy of 35 V. Details are discussed in Example 3.

Exemplary precursor ion spectra for lacosamide are found in FIG. 2. Exemplary fragmentation spectra of the lacosamide precursor ion with m/z of 251.0±0.5 are found in FIGS. 3A (collision energy of 20 V) and 3B (collision energy of 35 V).

Example 4: Intra-Assay and Inter-Assay Precision and Accuracy

Three quality control (QC) pools were prepared in the laboratory from drug-free serum, spiked with lacosamide to a concentration of 2.5, 5.0, and 15.0 µg/mL.

Five aliquots from each of the three QC pools were analyzed in a single assay, and each single assay repeated five times to determine the overall coefficient of variability (overall CV (%)) of a sample within an assay. All three controls (low, medium and high) met the acceptable reproducibility requirements of ≤10% CV. The sigma values on all controls were greater than 3.0, giving an acceptable precision. The Process Sigma based on the SD and % CV and the defined allowable total error (TEa) was calculated as:

Sigma (for precision only)=$TEa$ (units)/SD (units)= $TEa$ %/CV %

Calculated total error (TEc) was defined as a combination of imprecision and inaccuracy (or bias) and was calculated as $TEc=|bias|+m*SD$, where the multiplier "m" may have values of 2, 3, 4, even up to 6 (for Six Sigma performance) and SD is the total standard deviation of the method at or near the concentration where the bias was determined. Performance requirements and acceptability requirements may be derived from TEa. Precision, including Intra-Assay and Inter-Assay, the Total SD (or Total CV) must be <TEa/3.

The resulting 25 data points and summary of their analysis are presented in Table 2.

TABLE 2

Intra-Assay Variation and Accuracy for Laboratory Control

| | Run 1 | Run 2 | Run 3 | Run 4 | Run 5 |
|---|---|---|---|---|---|
| Level 1 | | | | | |
| Sample 1 | 2.57 | 2.60 | 2.46 | 2.47 | 2.52 |
| Sample 2 | 2.66 | 2.50 | 2.61 | 2.53 | 2.46 |
| Sample 3 | 2.55 | 2.58 | 2.57 | 2.47 | 2.49 |
| Sample 4 | 2.61 | 2.56 | 2.61 | 2.54 | 2.44 |
| Sample 5 | 2.62 | 2.64 | 2.59 | 2.55 | 2.59 |
| Count | 5 | 5 | 5 | 5 | 5 |
| Average | 2.60 | 2.58 | 2.57 | 2.51 | 2.50 |
| In-Run SD | 0.04 | 0.05 | 0.06 | 0.04 | 0.06 |

TABLE 2-continued

Intra-Assay Variation and Accuracy for Laboratory Control

Level 2

| Sample 1 | 5.21 | 5.14 | 4.89 | 5.07 | 5.14 |
|---|---|---|---|---|---|
| Sample 2 | 5.14 | 5.17 | 4.88 | 4.62 | 4.97 |
| Sample 3 | 5.08 | 5.32 | 4.88 | 4.74 | 5.16 |
| Sample 4 | 5.18 | 5.07 | 5.01 | 4.97 | 4.91 |
| Sample 5 | 5.23 | 5.15 | 4.90 | 4.89 | 4.97 |
| Count | 5 | 5 | 5 | 5 | 5 |
| Average | 5.17 | 5.17 | 4.91 | 4.86 | 5.03 |
| In-Run SD | 0.06 | 0.09 | 0.06 | 0.18 | 0.11 |

Level 3

| Sample 1 | 16.30 | 15.40 | 16.40 | 15.30 | 15.10 |
|---|---|---|---|---|---|
| Sample 2 | 16.20 | 15.90 | 16.20 | 15.80 | 15.80 |
| Sample 3 | 16.20 | 16.30 | 15.80 | 15.50 | 14.30 |
| Sample 4 | 16.10 | 16.00 | 15.70 | 16.00 | 14.80 |
| Sample 5 | 16.20 | 15.90 | 16.20 | 15.90 | 14.70 |
| Count | 5 | 5 | 5 | 5 | 5 |
| Average | 16.20 | 15.90 | 16.06 | 15.70 | 14.94 |
| In-Run SD | 0.07 | 0.32 | 0.30 | 0.29 | 0.56 |

Summary

|  | Level 1 | Level 2 | Level 3 |
|---|---|---|---|
| Count | 25 | 25 | 25 |
| Grand Mean | 2.55 | 5.03 | 15.76 |
| Pooled WR SD | 0.05 | 0.11 | 0.35 |
| Pooled WR CV | 2.03% | 2.18% | 2.19% |
| Overall SD | 0.06 | 0.16 | 0.55 |
| Overall CV | 2.43% | 3.27% | 3.49% |
| Sigma Overall | 10.31 | 7.63 | 7.15 |

Thirty-five aliquots from each of three additional QC pools custom-ordered from UTAK Laboratories at concentrations of 2.5, 5.0, and 12.0 µg/ml were assayed over three separate days (ten aliquots in two assays on day 1, fifteen aliquots in three assays on day 2, and ten aliquots in two assays on day 3) to determine the coefficient of variability (CV (%)) between assays. All controls met the acceptable reproducibility requirements of ≤10% CV. The results of these assays are presented in Table 3.

TABLE 3

Inter-Assay Variation and Accuracy for UTAK Controls

|  | Level I (2.5 µg/mL) | Level II (5.0 µg/mL) | Level III (12.0 µg/mL) |
|---|---|---|---|
| Mean | 2.89 | 5.74 | 12.21 |
| Standard Deviation | 0.20 | 0.45 | 0.85 |
| CV (%) | 6.89% | 7.85% | 6.94% |

Example 5: Analytical Sensitivity: Limit of Detection (LOD) and Lower Limit of Quantitation (LOQ)

The lower limit of quantitation (LOQ) is a measurement of selectivity, the ability of an analytical method to differentiate and quantify the analyte in the presence of other components in the sample. The LOQ was determined by assaying 20 replicates of serum diluent (i.e., blank). The LOQ was calculated as the mean of the blank assays plus 10 standard deviations (SD). The statistical LOQ for the lacosamide assay was determined to be 1 ng/mL.

The LOD is the point at which a value is beyond the uncertainty associated with its measurement and is defined as four standard deviations (SD) from the mean value of measuring zero concentration. To determine the LOD for the lacosamide assay, 20 replicates of serum diluent (i.e., blank) were statistically analyzed. The LOD for the lacosamide assay was determined to be about 0.5 ng/mL.

Example 6: Assay Reportable Range and Linearity

Figure 4:
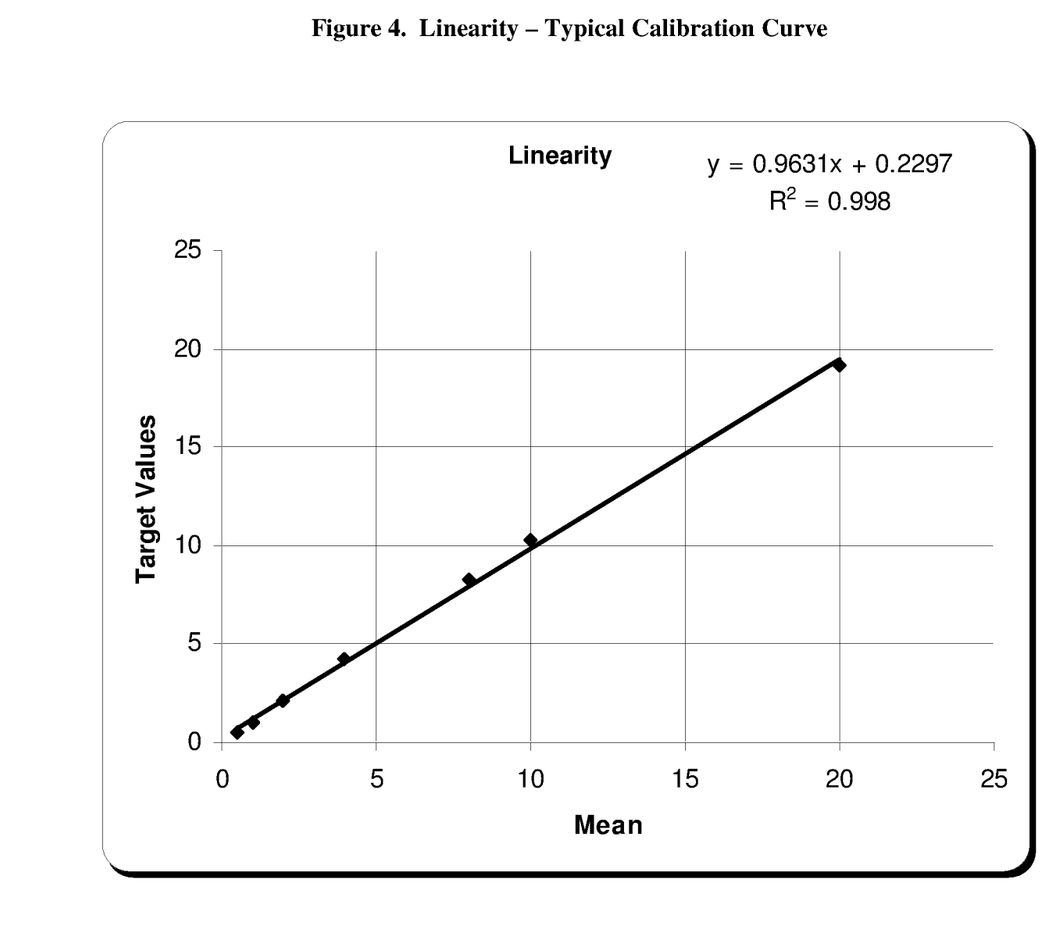
FIG. 4 shows the linearity of the quantitation of lacosamide in serially diluted stock samples using an LC-MS/MS assay. Details are described in Example 6.

To establish the linearity of lacosamide detection in the assay, seven standards with concentrations of 0.50 µg/ml, 1.00 µg/ml, 2.00 µg/ml, 4.00 µg/ml, 8.00 µg/ml, 10.00 µg/ml, and 20 µg/ml were run in duplicate within the same run. The results were plotted to show assay linearity, and are shown in FIG. 4. The assay is linear up to 20 µg/mL.

Example 7: Specimen Type Studies

Correlation studies were performed on spiked samples in different specimen types (serum, EDTA plasma, and Heparin plasma). The results of these studies are shown in Table 4.

TABLE 4

Comparison of Serum, EDTA Plasma and Heparin Plasma Sample Types

| Expected | Serum | | EDTA Plasma | | Heparin Plasma | |
|---|---|---|---|---|---|---|
| Value (µg/mL) | (µg/mL) | % Recovery | (µg/mL) | % Recovery | (µg/mL) | % Recovery |
| 2.63 | 2.64 | 100.32 | 2.73 | 103.74 | 2.81 | 106.78 |
| 3.03 | 3.05 | 100.65 | 2.97 | 98.01 | 3.10 | 102.30 |
| 3.92 | 4.01 | 102.26 | 3.93 | 100.22 | 3.95 | 100.73 |
| 4.44 | 4.60 | 103.50 | 4.42 | 99.45 | 4.97 | 111.83 |
| 5.56 | 5.77 | 103.86 | 6.12 | 110.16 | 5.81 | 104.58 |
| 5.97 | 6.09 | 102.01 | 6.28 | 105.19 | 6.12 | 102.51 |
| 6.45 | 6.78 | 105.09 | 6.67 | 103.39 | 6.82 | 105.71 |
| 7.02 | 7.20 | 102.60 | 7.48 | 106.59 | 7.34 | 104.60 |
| 8.51 | 8.95 | 105.16 | 9.09 | 106.81 | 8.76 | 102.93 |
| 9.09 | 9.60 | 105.60 | 10.40 | 114.40 | 9.94 | 109.34 |
| 10.81 | 11.00 | 101.75 | 11.10 | 102.68 | 11.50 | 106.38 |
| 12.50 | 13.10 | 104.80 | 13.40 | 107.20 | 13.60 | 108.80 |
| 13.33 | 13.60 | 102.00 | 13.50 | 101.25 | 13.50 | 101.25 |
| 14.81 | 15.00 | 101.25 | 15.50 | 104.63 | 15.00 | 101.25 |
| 18.18 | 18.70 | 102.85 | 18.50 | 101.75 | 19.20 | 105.60 |

Figure 5:
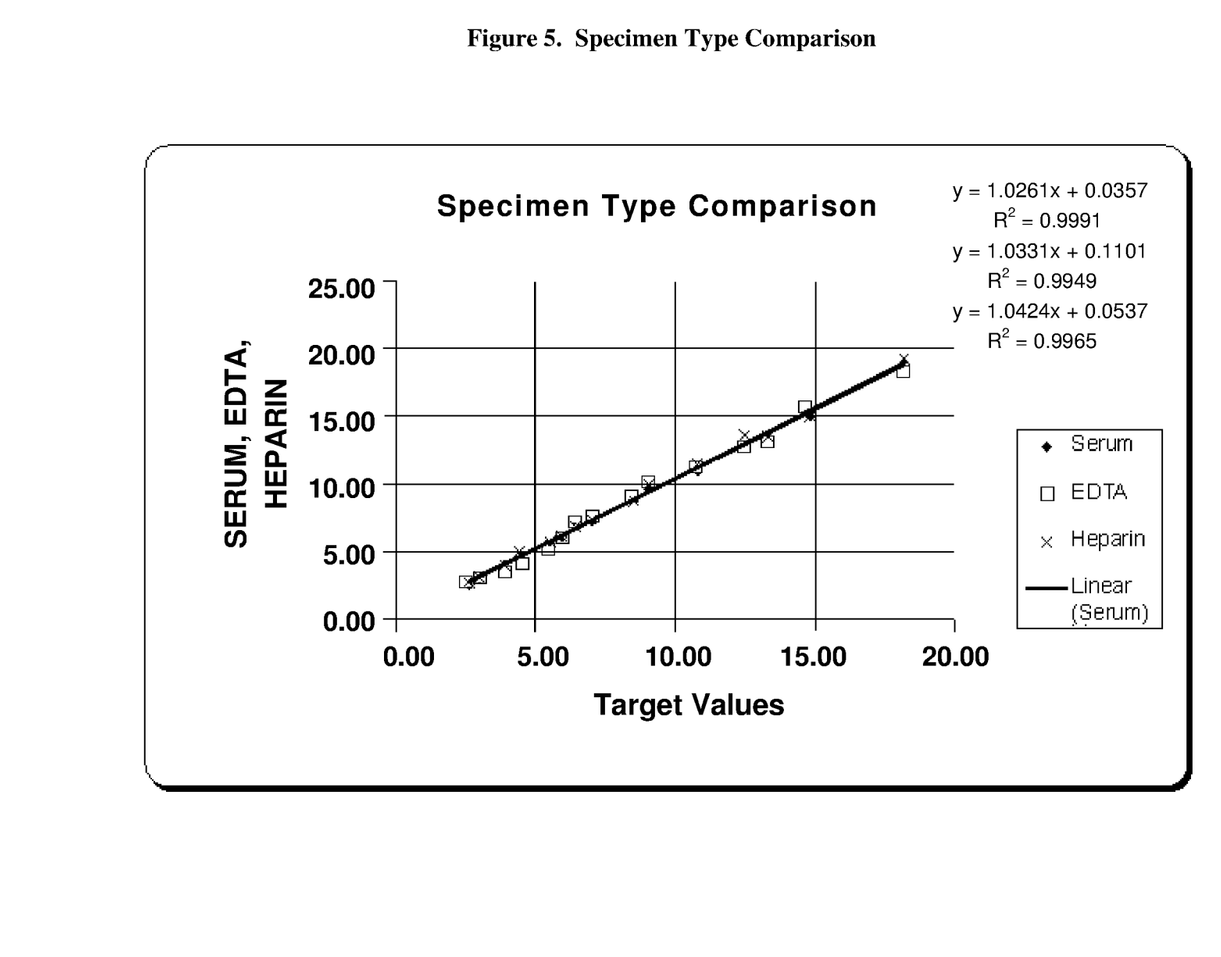
FIG. 5 shows a graph comparing lacosamide values in spiked samples of serum, EDTA, and heparin specimen types. Details are discussed in Example 7.

Results are presented graphically in FIG. 5. Serum data exhibited a $R^2$ value of 0.9991; EDTA Plasma exhibited a $R^2$ value of 0.9949; and Heparin Plasma exhibited a $R^2$ value of 0.9965. Thus, all tested specimen types are acceptable for analysis.

Example 8: Recovery

A recovery study of lacosamide in spiked serum was performed (in quadruplicate for the seven concentrations described in Example 6). Recovery of the QC material was acceptable for all concentrations tested (bias <TEa/4, assay slope=0.9710, and r=0.9994).

Example 9: Interference

An interference study was performed by introducing different concentrations of hemoglobin, triglycerides, and bilirubin into serum samples spiked with 2 µg/mL and 1.6 µg/mL of lacosamide. The samples were then subjected to HPLC-MS/MS as described in Example 3. Hemoglobin, triglycerides, and bilirubin did not significantly interfere with measurement of lacosamide in any of the samples tested. Tables 5 and 6 list the results for the interference study.

TABLE 5

Interference of Hemoglobin, Triglycerides, and Bilirubin with Detecting 2.0 µg/mL Lacosamide in Serum

| | 1st Result (µg/mL) | 2nd Result (µg/mL) | Average (µg/mL) | Recovery % |
|---|---|---|---|---|
| Hemoglobin | | | | |
| Neat | 1.91 | 1.85 | 1.88 | |
| High | 2.04 | 2.02 | 2.03 | 107.98 |
| Medium | 2.03 | 1.96 | 2.00 | 106.12 |
| Low | 1.99 | 2.00 | 2.00 | 106.12 |
| Triglycerides | | | | |
| Neat | 1.91 | 1.85 | 1.88 | |
| High | 1.83 | 1.85 | 1.84 | 97.87 |
| Medium | 1.90 | 1.97 | 1.94 | 102.93 |
| Low | 1.99 | 2.04 | 2.02 | 107.18 |
| Bilirubin | | | | |
| Neat | 1.91 | 1.85 | 1.88 | |
| High | 1.92 | 1.92 | 1.92 | 102.13 |
| Medium | 2.10 | 2.07 | 2.09 | 110.90 |
| Low | 2.03 | 1.99 | 2.01 | 106.91 |

TABLE 6

Interference of Hemoglobin, Triglycerides, and Bilirubin with Detecting 1.6 µg/mL Lacosamide in Serum

| | 1st Result (µg/mL) | 2nd Result (µg/mL) | Average (µg/mL) | Recovery % |
|---|---|---|---|---|
| Hemoglobin | | | | |
| Neat | 1.48 | 1.49 | 1.49 | |
| High | 1.60 | 1.59 | 1.60 | 107.41 |
| Medium | 1.60 | 1.64 | 1.62 | 109.09 |
| Low | 1.58 | 1.67 | 1.63 | 109.43 |
| Triglycerides | | | | |
| Neat | 1.48 | 1.49 | 1.49 | |
| High | 1.45 | 1.36 | 1.41 | 94.61 |
| Medium | 1.57 | 1.52 | 1.55 | 104.04 |
| Low | 1.60 | 1.60 | 1.60 | 107.74 |
| Bilirubin | | | | |
| Neat | 1.48 | 1.49 | 1.49 | |
| High | 1.55 | 1.61 | 1.58 | 106.40 |
| Medium | 1.58 | 1.57 | 1.58 | 106.06 |
| Low | 1.57 | 1.59 | 1.58 | 106.40 |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining the amount of lacosamide in a sample, said method comprising:
    a. subjecting the sample to protein precipitation;
    b. purifying lacosamide from said sample by high performance liquid chromatography (HPLC);
    c. ionizing lacosamide and an internal standard by electrospray ionization (ESI) to produce at least one lacosamide ion and at least one internal standard ion detectable by mass spectrometry, wherein the ions are fragmented with a collision energy of 35V;
    d. determining an amount of said at least one lacosamide ion and an amount of said at least one internal standard ion by mass spectrometry; and
    e. comparing the amount of said at least one lacosamide ion and the amount of said at least one internal standard ion to determine the amount of lacosamide in the sample.

2. The method of claim 1, wherein said mass spectrometry is tandem mass spectrometry.

3. The method of claim 1, wherein said sample is a body fluid.

4. The method of claim 1, wherein said sample is plasma or serum.

5. The method of claim 1, wherein said ionizing comprises generating a lacosamide precursor ion with a mass/charge ratio of 251.0±0.5, and generating one or more lacosamide fragment ions selected from the group consisting of ions with a mass/charge ratio of 91.0±0.5 and 108.0±0.5.

6. The method of claim 1, wherein said internal standard is lacosamide-D3.

7. The method of claim 1, wherein said ionizing comprises generating an internal standard precursor ion with a mass/charge ratio of 254.0±0.5, and generating an internal standard fragment ion with a mass/charge ratio of 91.0±0.5.

8. The method of claim 1, wherein said ionizing is conducted in positive ion mode.

9. A method for determining the amount of lacosamide in a sample, said method comprising:
    (i) subjecting the sample to protein precipitation;
    (ii) purifying lacosamide from said sample by high performance liquid chromatography (HPLC);
    (iii) ionizing lacosamide and an internal standard by electrospray ionization (ESI) to produce at least one lacosamide ion and at least one internal standard ion detectable by mass spectrometry, wherein the ions are fragmented with a collision energy of 35V;

(iv) determining an amount of said at least one lacosamide ion and an amount of said at least one internal standard ion by mass spectrometry; and (v) comparing the amount of said ions of (iv) determined by mass spectrometry to determine the amount of lacosamide in the sample.

10. The method of claim 9, wherein said mass spectrometry is tandem mass spectrometry.

11. The method of claim 9, wherein said sample is a body fluid.

12. The method of claim 9, wherein said sample is plasma or serum.

13. The method of claim 9, wherein said ionizing comprises generating a lacosamide precursor ion with a mass/charge ratio of 251.0±0.5, and generating one or more lacosamide fragment ions selected from the group consisting of ions with a mass/charge ratio of 91.0±0.5 and 108.0±0.5.

14. The method of claim 9, wherein said internal standard is lacosamide-D3.

15. The method of claim 9, wherein said ionizing comprises generating an internal standard precursor ion with a mass/charge ratio of 254.0±0.5, and generating an internal standard fragment ion with a mass/charge ratio of 91.0±0.5.

16. The method of claim 9, wherein said ionizing is conducted in positive ion mode.

\* \* \* \* \*